(12) United States Patent
Sakamoto et al.

(10) Patent No.: US 8,697,695 B2
(45) Date of Patent: Apr. 15, 2014

(54) PEST CONTROL COMPOSITION

(75) Inventors: Norihisa Sakamoto, Sanda (JP); Shinya Nishimura, Yokohama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/500,443

(22) PCT Filed: Oct. 19, 2010

(86) PCT No.: PCT/JP2010/068799
§ 371 (c)(1),
(2), (4) Date: May 8, 2012

(87) PCT Pub. No.: WO2011/049233
PCT Pub. Date: Apr. 28, 2011

(65) Prior Publication Data
US 2012/0208853 A1    Aug. 16, 2012

(30) Foreign Application Priority Data

Oct. 23, 2009   (JP) .................. 2009-244230

(51) Int. Cl.
*A61K 31/5377*   (2006.01)

(52) U.S. Cl.
USPC ...................................... 514/235.8

(58) Field of Classification Search
None
See application file for complete search history.

(56) References Cited

U.S. PATENT DOCUMENTS

| | | | |
|---|---|---|---|
| 2008/0027046 A1 | 1/2008 | Annan et al. | |
| 2009/0104145 A1 | 4/2009 | Hughes et al. | |
| 2009/0181956 A1* | 7/2009 | Ikegami et al. | 514/227.8 |
| 2010/0145059 A1 | 6/2010 | Hirose et al. | |

FOREIGN PATENT DOCUMENTS

| | | |
|---|---|---|
| JP | 2007-182422 | 7/2007 |
| JP | 2008/505121 | 2/2008 |
| JP | 2008-507582 | 3/2008 |
| JP | 2009-046401 | 3/2009 |
| JP | 2010-222342 | 10/2010 |
| JP | 2010-222343 | 10/2010 |
| WO | 2006/007595 | 1/2006 |
| WO | 2006/068669 | 6/2006 |
| WO | 2008/126933 | 10/2008 |

OTHER PUBLICATIONS

International Search Report issued Nov. 16, 2010 in International (PCT) Application No. PCT/JP2010/068799, of which the present application is the national stage.
Supplementary European Search Report issued May 24, 2013 in corresponding European Application No. EP 10 82 5080.4.
"749 Pyriproxyfen", The Pesticide Manual—A World Compendium—15th Edition, Jan. 1, 2009, pp. 997-998.
Mexican Office Action issued Nov. 27, 2013 in corresponding Mexican Application No. MX/a/2012/004453 (with English translation).

* cited by examiner

*Primary Examiner* — San-Ming Hui
*Assistant Examiner* — Jeanmarie Calvillo
(74) *Attorney, Agent, or Firm* — Wenderoth, Lind & Ponack, L.L.P.

(57) ABSTRACT

The present invention provides a pest control composition comprising, as active ingredients, (A) an amide compound of the formula (I), wherein $R^1$ is an ethyl group, $R^2$ is a hydrogen atom or an ethyl group, $R^3$ is a methyl group, $R^4$ is a chlorine atom, a bromine atom or a methyl group, $R^5$ is a chlorine atom, a bromine atom or a cyano group, $R^6$ is a chlorine atom, a bromine atom or a trifluoromethyl group and $R^7$ is a chlorine atom; and (B) pyriproxyfen.

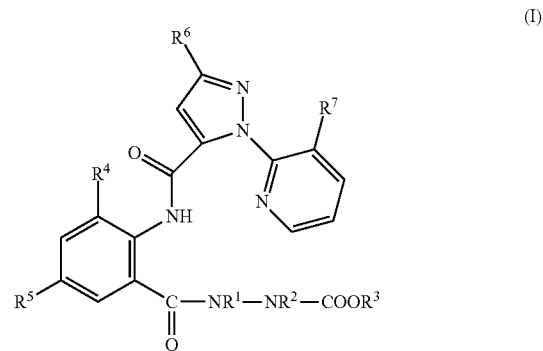

(I)

4 Claims, No Drawings

PEST CONTROL COMPOSITION

TECHNICAL FIELD

The present invention relates to a pest control composition.

BACKGROUND ART

Conventionally, a lot of compounds have been developed and put into practical use, for controlling pests (JP-A-2007-182422).

DISCLOSURE OF INVENTION

An object of the present invention is to provide a composition for controlling pests and a method for controlling pests and so on, having an excellent efficacy for controlling pests.

The present invention provides a pest control composition comprising, as active ingredients, the following (A) and (B) (hereinafter, referred to as composition of the present invention, in some cases):

(A) an amide compound of the formula (I):

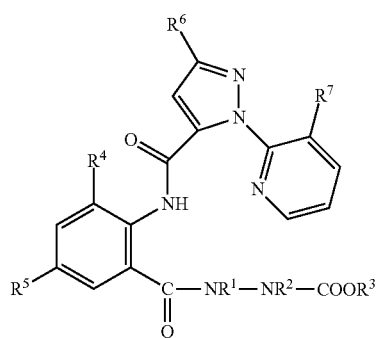

wherein, $R^1$ represents a C1-C6 alkyl group optionally substituted with one or more halogen atoms, $R^2$ represents a hydrogen atom or a C1-C6 alkyl group optionally substituted with one or more halogen atoms, $R^3$ represents a C1-C6 alkyl group optionally substituted with one or more halogen atoms, a C3-C6 alkoxyalkyl group optionally substituted with one or more halogen atoms, a C3-C6 alkenyl group optionally substituted with one or more halogen atoms or a C3-C6 alkynyl group optionally substituted with one or more halogen atoms, $R^4$ represents a halogen atom or a C1-C6 alkyl group optionally substituted with one or more halogen atoms, $R^5$ represents a hydrogen atom, a halogen atom, a cyano group or a C1-C6 alkyl group optionally substituted with one or more halogen atoms, $R^6$ represents a hydrogen atom, a halogen atom, a cyano group, a C1-C6 alkyl group optionally substituted with one or more halogen atoms, a C1-C6 alkoxy group optionally substituted with one or more halogen atoms, a C1-C6 alkylthio group optionally substituted with one or more halogen atoms, a C1-C6 alkylsulfinyl group optionally substituted with one or more halogen atoms or a C1-C6 alkylsulfonyl group optionally substituted with one or more halogen atoms, and $R^7$ represents a halogen atom or a C1-C6 alkyl group optionally substituted with one or more halogen atoms; and (B) pyriproxyfen.

Specifically, the present invention includes:

[1] a pest control composition comprising, as active ingredients, the following (A) and (B):

(A) an amide compound of the formula (I):

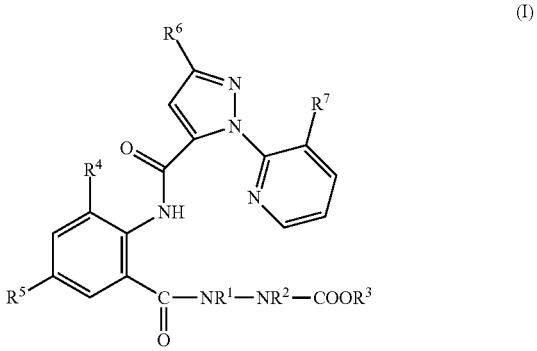

wherein, $R^1$ represents a C1-C6 alkyl group optionally substituted with one or more halogen atoms, $R^2$ represents a hydrogen atom or a C1-C6 alkyl group optionally substituted with one or more halogen atoms, $R^3$ represents a C1-C6 alkyl group optionally substituted with one or more halogen atoms, a C3-C6 alkoxyalkyl group optionally substituted with one or more halogen atoms, a C3-C6 alkenyl group optionally substituted with one or more halogen atoms or a C3-C6 alkynyl group optionally substituted with one or more halogen atoms, $R^4$ represents a halogen atom or a C1-C6 alkyl group optionally substituted with one or more halogen atoms, $R^5$ represents a hydrogen atom, a halogen atom, a cyano group or a C1-C6 alkyl group optionally substituted with one or more halogen atoms, $R^6$ represents a hydrogen atom, a halogen atom, a cyano group, a C1-C6 alkyl group optionally substituted with one or more halogen atoms, a C1-C6 alkoxy group optionally substituted with one or more halogen atoms, a C1-C6 alkylthio group optionally substituted with one or more halogen atoms, a C1-C6 alkylsulfinyl group optionally substituted with one or more halogen atoms or a C1-C6 alkylsulfonyl group optionally substituted with one or more halogen atoms, and $R^7$ represents a halogen atom or a C1-C6 alkyl group optionally substituted with one or more halogen atoms; and (B) pyriproxyfen;

[2] the pest control composition according to [1], wherein the weight ratio of the component (A) to the component (B) is 10:90 to 90:10;

[3] the pest control composition according to [1] or [2], wherein $R^1$ is a methyl group, ethyl group or isopropyl group, $R^2$ is a hydrogen atom, methyl group or ethyl group, $R^3$ is a methyl group or ethyl group, $R^4$ is a halogen atom or methyl group, $R^5$ is a halogen atom or cyano group, $R^6$ is a halogen atom or trifluoromethyl group and $R^7$ is a halogen atom, in the formula (I); and

[4] a pest control method comprising applying an effective amount of the pest control composition as defined in any one of [1] to [3] to a pest, a habitat of a pest, or a plant to be protected from damage by a pest.

The present invention is capable of providing a pest control composition showing an excellent efficacy for controlling pests.

MODES FOR CARRYING OUT THE INVENTION

The present invention will be described in detail below.

The component (A), that is, an amide compound of the formula (I):

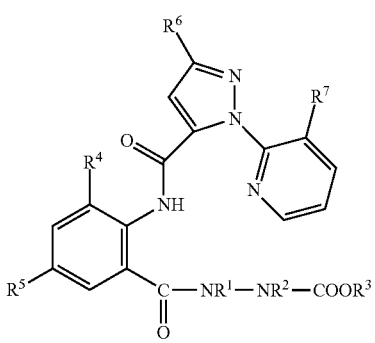

(I)

wherein, $R^1$ represents a C1-C6 alkyl group optionally substituted with one or more halogen atoms, $R^2$ represents a hydrogen atom or a C1-C6 alkyl group optionally substituted with one or more halogen atoms, $R^3$ represents a C1-C6 alkyl group optionally substituted with one or more halogen atoms, a C3-C6 alkoxyalkyl group optionally substituted with one or more halogen atoms, a C3-C6 alkenyl group optionally substituted with one or more halogen atoms or a C3-C6 alkynyl group optionally substituted with one or more halogen atoms, $R^4$ represents a halogen atom or a C1-C6 alkyl group optionally substituted with one or more halogen atoms, $R^5$ represents a hydrogen atom, a halogen atom, a cyano group or a C1-C6 alkyl group optionally substituted with one or more halogen atoms, $R^6$ represents a hydrogen atom, a halogen atom, a cyano group, a C1-C6 alkyl group optionally substituted with one or more halogen atoms, a C1-C6 alkoxy group optionally substituted with one or more halogen atoms, a C1-C6 alkylthio group optionally substituted with one or more halogen atoms, a C1-C6 alkylsulfinyl group optionally substituted with one or more halogen atoms or a C1-C6 alkylsulfonyl group optionally substituted with one or more halogen atoms, and $R^7$ represents a halogen atom or a C1-C6 alkyl group optionally substituted with one or more halogen atoms; (hereinafter, referred to as the amide compound (I) in some cases) will be explained.

For substituents represented by $R^1$ to $R^7$ in the formula (I):

Examples of "halogen atom" include a fluorine atom, chlorine atom, bromine atom and iodine atom.

Examples of "C1-C6 alkyl group optionally substituted with one or more halogen atoms" include a methyl group, trifluoromethyl group, trichloromethyl group, chloromethyl group, dichloromethyl group, fluoromethyl group, difluoromethyl group, ethyl group, pentafluoroethyl group, 2,2,2-trifluoroethyl group, 2,2,2-trichloroethyl group, propyl group, isopropyl group, heptafluoroisopropyl group, butyl group, isobutyl group, sec-butyl group, tert-butyl group, pentyl group and hexyl group.

Examples of "C3-C6 alkoxyalkyl group optionally substituted with one or more halogen atoms" include a 2-methoxyethyl group, 2-ethoxyethyl group and 2-isopropyloxyethyl group.

Examples of "C2-C6 alkenyl group optionally substituted with one or more halogen atoms" include a 2-propenyl group, 3-chloro-2-propenyl group, 2-chloro-2-propenyl group, 3,3-dichloro-2-propenyl group, 2-butenyl group, 3-butenyl group, 2-methyl-2-propenyl group, 3-methyl-2-butenyl group, 2-pentenyl group and 2-hexenyl group.

Examples of "C3-C6 alkynyl group optionally substituted with one or more halogen atoms" include a 2-propynyl group, 3-chloro-2-propynyl group, 3-bromo-2-propynyl group, 2-butynyl group and 3-butynyl group.

Examples of "C1-C6 alkoxy group optionally substituted with one or more halogen atoms" include a methoxy group, ethoxy group, 2,2,2-trifluoroethoxy group, propoxy group, isopropyloxy group, butoxy group, isobutyloxy group, sec-butoxy group and tert-butoxy group.

Examples of "C1-C6 alkylthio group optionally substituted with one or more halogen atoms" include a methylthio group, trifluoromethylthio group, ethylthio group, propylthio group, isopropylthio group, butylthio group, isobutylthio group, sec-butylthio group, tert-butylthio group, pentylthio group and hexylthio group.

Examples of "C1-C6 alkylsulfinyl group optionally substituted with one or more halogen atoms" include a methylsulfinyl group, trifluoromethylsulfinyl group, ethylsulfinyl group, propylsulfinyl group, isopropylsulfinyl group, butylsulfinyl group, isobutylsulfinyl group, sec-butylsulfinyl group, tert-butylsulfinyl group, pentylsulfinyl group and hexylsulfinyl group.

Examples of "C1-C6 alkylsulfonyl group optionally substituted with one or more halogen atoms" include a methylsulfonyl group, trifluoromethylsulfonyl group, ethylsulfonyl group, propylsulfonyl group, isopropylsulfonyl group, butylsulfonyl group, isobutylsulfonyl group, sec-butylsulfonyl group, tert-butylsulfonyl group, pentylsulfonyl group and hexylsulfonyl group.

Embodiments of the amide compound (I) include, for example, compounds of the formula (I) in which $R^1$ is a methyl group, ethyl group or isopropyl group, $R^2$ is a hydrogen atom, methyl group or ethyl group, $R^3$ is a methyl group or ethyl group, $R^4$ is a halogen atom or methyl group, $R^5$ is a halogen atom or cyano group, $R^6$ is a halogen atom or trifluoromethyl group and $R^7$ is a halogen atom. As the component (A), these compounds may be used singly, or a mixture of two amide compounds (I) may be used.

Preferable embodiments of the amide compound (I) include:

a compound of the formula (I) in which $R^1$ is an ethyl group, $R^2$ is a hydrogen atom, $R^3$ is a methyl group, $R^4$ is a chlorine atom, bromine atom or methyl group, $R^5$ is a chlorine atom, bromine atom or cyano group, $R^6$ is a chlorine atom, bromine atom or trifluoromethyl group and $R^7$ is a chlorine atom;

a compound of the formula (I) in which $R^1$ is an ethyl group, $R^2$ is an ethyl group, $R^3$ is a methyl group, $R^4$ is a chlorine atom, bromine atom or methyl group, $R^5$ is a chlorine atom, bromine atom or cyano group, $R^6$ is a chlorine atom, bromine atom or trifluoromethyl group and $R^7$ is a chlorine atom; and a compound of the formula (I) in which $R^1$ is an ethyl group, $R^2$ is a hydrogen atom, $R^3$ is a methyl group, $R^4$ is a bromine atom or methyl group, $R^5$ is a bromine atom or cyano group, $R^6$ is a chlorine atom or bromine atom and $R^7$ is a chlorine atom.

Specific examples of the amide compound (I) are shown in Tables 1 and 2.

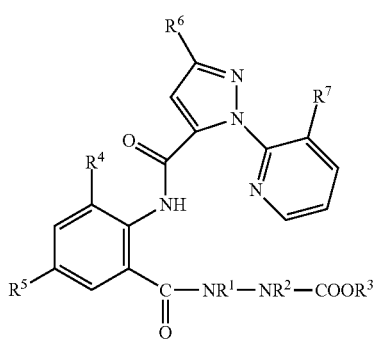

(I)

TABLE 1

| Compound No. | $R^1$ | $R^2$ | $R^3$ | $R^4$ | $R^5$ | $R^6$ | $R^7$ |
|---|---|---|---|---|---|---|---|
| 1 | $CH_3CH_2$ | H | $CH_3$ | Br | Br | Br | Cl |
| 2 | $(CH_3)_2CH$ | H | $CH_3$ | Br | Br | Br | Cl |
| 3 | $CH_3$ | H | $CH_3CH_2$ | Cl | Cl | Br | Cl |
| 4 | $CH_3$ | $CH_3$ | $CH_3$ | Br | Cl | Br | Cl |
| 5 | $CH_3$ | $CH_3$ | $CH_3$ | $CH_3$ | Cl | Cl | Cl |
| 6 | $CH_3$ | $CH_3$ | $CH_3$ | Cl | Cl | Cl | Cl |
| 7 | $CH_3$ | $CH_3$ | $CH_3$ | Br | Br | Cl | Cl |
| 8 | $CH_3CH_2$ | H | $CH_3$ | Cl | Cl | Br | Cl |
| 9 | $CH_3$ | $CH_3$ | $CH_3$ | Br | Br | $CF_3$ | Cl |
| 10 | $CH_3(CH_2)_2$ | H | $CH_3$ | Br | Br | Br | Cl |
| 11 | $CH_3$ | $CH_3CH_2$ | $CH_3$ | Br | Br | Br | Cl |
| 12 | $CH_3CH_2$ | $CH_3$ | $CH_3$ | Br | Br | Br | Cl |
| 13 | $CH_3CH_2$ | $CH_3CH_2$ | $CH_3$ | Br | Br | Br | Cl |
| 14 | $CH_3CH_2$ | H | $CH_3$ | $CH_3$ | Cl | Br | Cl |
| 15 | $CH_3CH_2$ | H | $CH_3$ | $CH_3$ | CN | Br | Cl |
| 16 | $CH_3CH_2$ | H | $CH_3$ | Br | Br | Cl | Cl |

TABLE 2

| Compound No. | $R^1$ | $R^2$ | $R^3$ | $R^4$ | $R^5$ | $R^6$ | $R^7$ |
|---|---|---|---|---|---|---|---|
| 17 | $CH_3CH_2$ | H | $CH_3$ | Cl | Cl | Cl | Cl |
| 18 | $CH_3CH_2$ | H | $CH_3$ | $CH_3$ | Cl | Cl | Cl |
| 19 | $CH_3CH_2$ | H | $CH_3$ | $CH_3$ | CN | Cl | Cl |
| 20 | $CH_3CH_2$ | H | $CH_3$ | Br | Br | $CF_3$ | Cl |
| 21 | $CH_3CH_2$ | H | $CH_3$ | Cl | Cl | $CF_3$ | Cl |
| 22 | $CH_3CH_2$ | H | $CH_3$ | $CH_3$ | Cl | $CF_3$ | Cl |
| 23 | $CH_3CH_2$ | H | $CH_3$ | $CH_3$ C | N | $CF_3$ | Cl |
| 24 | $CH_3$ | H | $CH_3$ | Br | Br | $CF_3$ | Cl |
| 25 | $CH_3$ | H | $CH_3$ | Br | Br | Cl | Cl |
| 26 | $CH_3$ | H | $CH_3$ | Cl | Cl | Cl | Cl |
| 27 | $CH_3$ | H | $CH_3$ | $CH_3$ | Cl | Cl | Cl |
| 28 | $CH_3$ | H | $CH_3$ | $CH_3$ | CN | Cl | Cl |
| 29 | $CH_3$ | H | $CH_3$ | Cl | Cl | $CF_3$ | Cl |
| 30 | $CH_3$ | H | $CH_3$ | $CH_3$ | CN | $CF_3$ | Cl |
| 31 | $CH_3$ | $CH_3$ | $CH_3$ | $CH_3$ | CN | Cl | Cl |
| 32 | $CH_3$ | $CH_3$ | $CH_3$ | Cl | Cl | $CF_3$ | Cl |
| 33 | $CH_3$ | $CH_3$ | $CH_3$ | $CH_3$ | Cl | $CF_3$ | Cl |
| 34 | $CH_3$ | $CH_3$ | $CH_3$ | $CH_3$ | CN | $CF_3$ | Cl |

The amide compound (I) can be produced by methods described in JP-A No. 2007-182422 and JP-A No. 2008-280335.

The component (B), that is, pyriproxyfen will be described.

Pyriproxyfen (chemical name: 4-phenoxyphenyl (RS)-2-(2-pyridyloxy)propyl ether) is described in "The Pesticide Manual, Fourteenth Edition" (edited by Clive Tomlin, published by The British Crop Protection Council and The Royal Society of Chemistry, 2006), p. 923 and is commercially available.

For the component (A) and the component (B), stereoisomers thereof may exist respectively, and the present invention includes these stereoisomers and mixture of these stereoisomers.

The component (A) and the component (B) may form agrichemically acceptable salts, respectively. Examples of these salts include salts with inorganic bases (for example, alkali metals such as sodium, potassium and lithium, alkaline earth metals such as calcium and magnesium, and ammonia), organic bases (for example, pyridine, collidine, triethylamine and triethanolamine), inorganic acids (for example, hydrochloric acid, hydrobromic acid, hydroiodic acid, phosphoric acid, sulfuric acid and perchloric acid), organic acids (for example, formic acid, acetic acid, tartaric acid, malic acid, citric acid, oxalic acid, succinic acid, benzoic acid, picric acid, methanesulfonic acid and p-toluenesulfonic acid).

The composition of the present invention can be prepared into a dosage form such as emulsion agent, liquid agent, micro emulsion agent, flowable agent, oil agent, wettable powder agent, powder agent, granule agent, fine granule agent, seed coating agent, seed immersion agent, smoking agent, tablet agent, microcapsule agent, spray agent, aerosol agent, carbon dioxide gas preparation, EW agent, ointment, capsule agent, pellet agent, injection agent and coating agent, for example, by dissolving or dispersing the component (A) and the component (B) of the composition in a suitable liquid carrier, or mixing the components with or allowing the components to be adsorbed on a suitable solid carrier.

If necessary, for example, a gaseous carrier, ointment base, surfactant, or other additives may be added to these preparations, and these can be prepared by known methods.

Examples of the liquid carrier include water, alcohols (for example, methyl alcohol, ethyl alcohol, n-propyl alcohol, isopropyl alcohol, butyl alcohol, hexyl alcohol, benzyl alcohol, ethylene glycol, propylene glycol and phenoxyethanol), ketones (for example, acetone, methyl ethyl ketone, methyl isobutyl ketone and cyclohexanone), ethers (for example, diisopropyl ether, 1,4-dioxane, tetrahydrofuran, ethylene glycol monomethyl ether, ethylene glycol dimethyl ether, diethylene glycol monomethyl ether, propylene glycol monomethyl ether, dipropylene glycol monomethyl ether and 3-methoxy-3-methyl-1-butanol), aliphatic hydrocarbons (for example, hexane, cyclohexane, kerosene, lamp oil, fuel oil and machine oil), aromatic hydrocarbons (for example, toluene, xylene, ethylbenzene, dodecylbenzene, phenylxylylethane, solvent naphtha and methylnaphthalene), halogenated hydrocarbons (for example, dichloromethane, trichloroethane, chloroform and carbon tetrachloride), acid amides (for example, N,N-dimethylformamide, N,N-dimethylacetamide, N-methylpyrrolidone and N-octylpyrrolidone), esters (for example, butyl lactate, ethyl acetate, butyl acetate, isopropyl myristate, ethyl oleate, diisopropyl adipate, diisobutyl adipate, propylene glycol monomethyl ether acetate, fatty acid glycerin ester and γ-butyrolactone), nitriles (for example, acetonitrile, isobutyronitrile and propionitrile), carbonates (for example, propylene carbonate) and vegetable oils (for example, soybean oil, olive oil, linseed oil, coconut oil, palm oil, peanut oil, malt oil, almond oil, sesame oil, mineral oil, rosmarinic oil, geranium oil, rapeseed oil, cotton seed oil, corn oil, safflower oil and orange oil), and these liquid carriers may be mixed at suitable proportion and used (preferably, one or more and three or less are used).

Examples of the solid carrier (dilution agent, extending agent) include plant powders (for example, soybean flour, tobacco flour, wheat flour and wood flour), mineral powders (for example, clays such as kaolin clay, Fubasami clay, bentonite and acid clay, talcs such as talc powder and agalmatolite powder, silicas such as white carbon, diatomaceous earth and mica powder), synthetic hydrated silicon oxide, alumina, talc, ceramic, other inorganic minerals (sericite, quartz, sulfur, active carbon, calcium carbonate and hydrated silica) and chemical fertilizers (ammonium sulfate, ammonium phosphate, ammonium nitrate, urea and ammonium chloride) in the form of fine powder and granule, and these solid carriers may be mixed at suitable proportion and used (preferably, one or more and three or less are used).

As the gaseous carrier which can be used in the above-described preparations, for example, fluorocarbon, butane gas, LPG (liquefied petroleum gas), dimethyl ether and carbon dioxide gas are mentioned, and these gaseous carriers can be used singly or two of them can be mixed in suitable proportion, or can be combined with a suitable liquid carrier, and used.

Examples of the ointment base include polyethylene glycol, pectine, polyhydric alcohol esters of higher fatty acids (for example, monostearic acid glycerin ester), cellulose derivatives (for example, methylcellulose), sodium alginate, bentonite, higher alcohols, polyhydric alcohols (for example, glycerin), vaseline, white vaseline, liquid paraffin, lard, various vegetable oils, lanolin, dehydrated lanolin, hardened oil and resins, and these ointment bases may be used in combination (preferably, one or more and three or less are used), or surfactants shown below can be added to them.

Examples of the surfactant include nonionic and anionic surfactants such as soaps, polyoxyethylene alkyl aryl ethers (for example, Noigen (product name, registered trademark, manufactured by Dai-Ichi Kogyo Seiyaku Co., Ltd.), EA142 (EA142 (product name, manufactured by Dai-Ichi Kogyo Seiyaku Co., Ltd.)), Nonal (product name, manufactured by Toho Chemical Industry Co., Ltd.)), polyoxyethylene tristyrylphenyl ether phosphoric acid (for example, Soprophor (registered trademark) FLK (product name, manufactured by Rhodia Nikka Co., Ltd.)), alkylsulfates (for example, Emal 10 (product name, registered trademark, manufactured by Kao Corporation), Emal 40 (product name, registered trademark, manufactured by Kao Corporation), sodium lauryl sulfate), alkylbenzene sulfonates (for example, Neogen (product name, registered trademark, manufactured by Dai-Ichi Kogyo Seiyaku Co., Ltd.), Neogen T (product name, registered trademark, manufactured by Dai-Ichi Kogyo Seiyaku Co., Ltd.), Neopelex (product name, registered trademark, manufactured by Kao Corporation), BC2070M (product name, manufactured by TAYCA Corporation)), polyethylene glycol ethers (for example, Nonipole 85 (product name, registered trademark, manufactured by Sanyo Chemical Industries, Ltd.), Nonipole 100 (product name, registered trademark, manufactured by Sanyo Chemical Industries, Ltd.), Nonipole 160 (product name, registered trademark, manufactured by Sanyo Chemical Industries, Ltd.)), polyoxyethylene alkyl ethers (for example, Noigen ET-135 (product name, registered trademark, manufactured by Dai-Ichi Kogyo Seiyaku Co., Ltd.)), polyoxyethylene polyoxypropylene block polymers (for example, Newpole PE-64 (product name, registered trademark, manufactured by Sanyo Chemical Industries, Ltd.)), polyhydric alcohol esters (for example, Tween 20 (product name, registered trademark, manufactured by Kao Corporation), Tween 80 (product name, registered trademark, manufactured by Kao Corporation)), alkylsulfosuccinates (for example, Sanmorin OT20 (product name, registered trademark, manufactured by Sanyo Chemical Industries, Ltd.), Newcalgen EX70 (product name, manufactured by TAKEMOTO Oil & Fat Co., Ltd.)), alkyl aryl sulfonates (for example, Newcalgen WG-1 (product name, manufactured by TAKEMOTO Oil & Fat Co., Ltd.), Morwet EFW (product name, manufactured by DESOTO, Inc.), alkenyl sulfonates (for example, Sorpole 5115 (product name, registered trademark, manufactured by Toho Chemical Industry Co., Ltd.)) and calcium lignin sulfonate, and these surfactants can be mixed in suitable proportion and used (preferably, one or more and three or less are used).

Examples of the other additives include casein, gelatin, saccharides (starch, xanthan gum, gum arabic, cellulose derivatives and alginic acid), lignin derivatives, bentonite, synthetic water-soluble polymers (polyvinyl alcohol, polyvinyl pyrrolidone, and polyacrylic acids), PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), aluminum magnesium silicate, dyes (for example, FLEXIVERSE (registered trademark, product name, manufactured by Sun Chemical)), preservatives (for example, Proxel (registered trademark) GXL (product name, manufactured by Arch Chemicals Inc.)), emulsifiers (for example, sorbitan trioleate), defoaming agents (for example, Antifoam C Emulsion (product name, registered trademark; manufactured by Dow Corning)) and dispersing agents (for example, Morwet D425 (product name, manufactured by AkzoNobel)).

In the composition of the present invention, the weight ratio of the component (A) to the component (B) is usually 1:99 to 99:1, preferably 10:90 to 90:10, more preferably 30:70 to 60:40.

The content of additives other than the above-described active ingredients varies depending on the kind or content of the active ingredients, or the form of the preparation, and it is usually about 0.001 to 99.9 wt %, preferably about 1 to 99 wt %. More specifically, it is desirable to add a surfactant in an amount of usually about 1 to 30 wt %, preferably about 1 to 15 wt %, a flow aid in an amount of usually about 1 to 20 wt %, a carrier in an amount of usually about 1 to 90 wt %, preferably about 1 to 70 wt %, with respect to the total amount of the composition. In the case of production of a liquid agent, it is desirable to add a surfactant in an amount of usually about 1 to 20 wt %, preferably about 1 to 10 wt % and water in an amount of about 20 to 90 wt %. In the case of production of an emulsion agent, it is desirable to add a surfactant in an amount of usually 1 to 30 wt %, preferably 2 to 15 wt % and an organic solvent. In the case of production of a granule wettable powder agent, it is desirable to add a surfactant in an amount of usually 0.1 to 10 wt %, preferably 0.5 to 5 wt %, a binder in an amount of usually 0.1 to 15 wt %, preferably 0.5 to 5 wt %, and an extending agent such as lactose, ammonium sulfate and orclay. In the case of production of a granule agent, it is desirable to add a surfactant in an amount of usually 0.1 to 10 wt %, preferably 0.5 to 5 wt %, a stabilizer in an amount of usually 0.1 to 10 wt %, preferably 0.5 to 5 wt %, and an extending agent such as clay. In the case of production of a Jumbo agent, it is desirable to add a surfactant in an amount of usually 0.1 to 15 wt %, preferably 0.5 to 5 wt %, a binder in an amount of usually 0.5 to 10 wt %, preferably 0.5 to 5 wt %, a floatation agent in an amount of usually 0.5 to 40 wt %, preferably 1 to 20 wt %, and an extending agent such as clay.

In use of the composition of the present invention, for example, the component (A) and the component (B) are applied in a proportion of usually 0.001 to 1000 g, preferably 0.01 to 100 g per 1000 $m^2$ of the application area. When the composition of the present invention is prepared into an emulsion agent, wettable powder agent, flowable agent, microcapsule agent or the like, the composition is diluted with water so as to give a concentration of the component (A) and the component (B) of usually 0.001 to 10000 ppm, preferably 0.01 to 500 ppm and applied, and when prepared into a granule agent, powder agent or the like, the composition is applied as it is.

Examples of the use method of the composition of the present invention include such methods of application as a spray treatment, soil treatment, seed treatment and hydroponic liquid treatment.

The spray treatment means, specifically, a treatment method in which pests harming a plant are controlled by applying an active ingredient to the plant surface, such as foliar spray and trunk spray.

The soil treatment means, for example, a treatment method in which the root zone of a crop plant is treated with an active ingredient to exert a control effect directly on pests present in the root zone, or an active ingredient is allowed to permeate and transfer into a plant through a root part or the like, thereby manifesting a control effect on pests harming the plant, and specific examples thereof include planting hole application, plant foot application, planting furrow application, planting row application, planting row application at sowing, broadcast application, side row application, water surface application, nursery box application and bed soil incorporation application.

The seed treatment means, for example, a treatment method in which an active ingredient is applied directly to crop seeds, seed tuber or bulb, or parts around them, thereby manifesting a control effect on pests harming the plant, and specific examples thereof include a spray treatment, smear treatment, immersion treatment, impregnation treatment, coating treatment, film coat treatment and pellet coat treatment.

The hydroponic liquid treatment means, for example, a treatment method in which an active ingredient is added to a hydroponic liquid and the like for allowing the active ingredient to permeate and transfer into a crop plant through a root part or the like, thereby manifesting a control effect on pests harming the plant, and specific examples thereof include hydroponic liquid incorporation and hydroponic liquid interfusion.

The composition of the present invention may contain other pest control active ingredients, for example, insecticides (for example, pyrethroid insecticide, organophosphorus insecticide, carbamate insecticide, nerve sodium channel blocker, insecticidal macrocyclic lactone, γ-aminobutyric acid (GABA) antagonist and calcium channel activatorurea insecticide, insect hormone mimic, natural insecticide, acaricide, nematocide, herbicide, plant hormone, other plant growth regulators, fungicides (for example, copper fungicide, organic chlorine fungicide, organic sulfur fungicide and phenol fungicide), synergist, attractant, repellent, drug adverse effect mitigating agent, dye, fertilizer, and soil improving agent.

The composition of the present invention can be used as a pest control agent for protecting plants in agricultural lands such as fields, rice fields, lawns and orchards or in non-agricultural lands.

Examples of the plant to be protected include the following plants.

Crops:
corn, rice, wheat, barley, rye, oat, sorghum, cotton, soybean, peanut, buckwheat, beet, rapeseed, sunflower, sugar cane, tobacco, and so on.

Vegetables:
solanaceous vegetables such as eggplant, tomato, pimento, pepper and potato;
cucurbitaceous vegetables such as cucumber, pumpkin, zucchini, water melon, melon and squash;
cruciferous vegetables such as Japanese radish, white turnip, horseradish, kohlrabi, Chinese cabbage, cabbage, leaf mustard, broccoli and cauliflower;
asteraceous vegetables such as burdock, crown daisy, artichoke and lettuce;
liliaceous vegetables such as green onion, onion, garlic and asparagus;
ammiaceous vegetables such as carrot, parsley, celery and parsnip; chenopodiaceous vegetables such as spinach and Swiss chard;
lamiaceous vegetables such as *Perilla frutescens*, mint and basil;
strawberry, sweet potato, Dioscorea japonica, colocasia, and so on.

Fruits:
pomaceous fruits such as apple, pear, Japanese pear, Chinese quince and quince;
stone fleshy fruits such as peach, plum, nectarine, *Prunus mume*, cherry fruit, apricot and prune;
citrus fruits such as *Citrus unshiu*, orange, lemon, rime and grapefruit;
nuts such as chestnuts, walnuts, hazelnuts, almond, pistachio, cashew nuts and *macadamia* nuts;
berries such as blueberry, cranberry, blackberry and raspberry;
grape, kaki fruit, olive, Japanese plum, banana, coffee, date palm, coconuts, oil palm, and so on.

Trees other than fruit trees:
tea, mulberry, flowering plant,
roadside trees such as ash, birch, dogwood, Eucalyptus, *Ginkgo biloba*, lilac, maple, *Quercus*, poplar, Judas tree, Liquidambar formosana, plane tree, zelkova, Japanese arborvitae, fir wood, hemlock, juniper, *Pinus, Picea* and Taxus cuspidate;
Jatropha, and so on.

Grasses:
zoysia such as *Zoysia japonica* and *Zoysia matrella*; bermudagrass (Cynodon) such as *Cynodon dactylon;*
bentgrass (Agrostis) such as *Agrostis alba, Agrostis stolonifera L., Agrostis tennis* Sibth.;
bluegrass (Poa) such as *Poa pratensis* L. and *Poa trivialis* L.;
fesucue (Festuca) such as *Festuca arundinacea* Schreb., *Festuca rubra* L. var. *commutata* Gaud. and *Festuca rubra* L. var. genuina Hack;
ryegrass (Lolium) such as *Lolium multiflorum* and *Lolium perenne;*
*Dactylis glomerata; Phleum pratense*; and so on.

Others:
bio-fuel plants such as *Jatropha curcas*, safflower, *Camelina*, switch grass, *Miscanthus giganteus, Phalaris arundinacea* L., *Arundo donax*, Kenaf (*Hibiscus cannabinus*), cassava (*Manihot esculenta*), Salicaceae and algae;
flowers; ornamental foliage plant; and so on.

The aforementioned "plants" include plants, to which tolerance to 4-hydroxyphenylpyruvate dioxygenase inhibitors such as isoxaflutole, acetolactate synthase (hereinafter, referred to as ALS) inhibitors such as imazethapyr and thifensulfuron-methyl, EPSP synthetase inhibitors such as glyphosate, glutamine synthetase inhibitors such as glufosinate, acetyl-CoA carboxylase inhibitors such as sethoxydim, protoporphyrinogen oxidase inhibitors such as flumioxazin, auxin type herbicides such as dicamba and 2,4-D and herbicides such as bromoxynil, has been conferred by a classical breeding method or by genetic engineering techniques.

Examples of a "plant" on which tolerance has been conferred by a classical breeding method include rape, wheat, sunflower, rice and corn tolerant to imidazolinone ALS inhibitory herbicides such as imazethapyr, which are already commercially available under a product name of Clearfield (registered trademark). Similarly, there is a soybean on which tolerance to sulfonylurea ALS inhibitory herbicides such as thifensulfuron-methyl has been conferred by a classical breeding method, which is already commercially available under a product name of STS soybean.

Examples of a plant on which tolerance to acetyl-CoA carboxylase inhibitors such as trione oxime or aryloxy phenoxypropionic acid herbicides has been conferred by a classical breeding method include SR corn. The plant on which tolerance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase tolerant to an acetyl-CoA carboxylase inhibitor is reported in Weed Science, vol. 53, pp. 728-746 (2005) and a plant tolerant to acetyl-CoA carboxylase inhibitors can be generated by introducing a gene of such an acetyl-CoA carboxylase variation into a plant by genetically engineering technology, or by introducing a variation conferring tolerance into a plant acetyl-CoA carboxylase.

Examples of a plant on which resistance has been conferred by a classical breeding method include crops resistant to nematode or aphid, specifically, a soybean into which RAG1 (Resistance Aphid Gene 1) gene that confers resistance to aphid has been introduced.

Plants tolerant to acetyl-CoA carboxylase inhibitors or ALS inhibitors or the like can be generated by introducing into the plant cell a nucleic acid for introduction of base-substitution variation represented by Chimeraplasty Technique (Gura T. 1999. Repairing the Genome's Spelling Mistakes. Science 285: 316-318) to introduce a site-directed amino acid substitution variation into an acetyl-CoA carboxylase gene or an ALS gene of the plant.

Crops such as a soybean tolerant to dicamba can be generated by introducing into the crops a gene encoding dicamba-degrading enzyme that includes dicamba monooxygenase isolated from *Pseudomonas maltophilia* (Behrens et al., 2007. Dicamba Resistance: Enlarging and Preserving Biotechnology-Based Weed Management Strategies. Science 316:1185-1188).

Crops tolerant to both of the following herbicides: phenoxypropionic acid herbicide such as 2,4-D, MCPA, Dichlorpropand Mecoprop; and
phenoxypropionic acid herbicide such as Quizalofop, Haloxyfop, Fluazifopm, Dichlorprop, Fenoxaprop, Metamifop, Cyhalofop and Clodinafop;
can be generated by introducing to the crops a gene encoding aryloxyalkanoate dioxygenase (WO2005/107437, WO2007/053482, WO2008/141154).

Examples of a plant on which tolerance has been conferred by genetic engineering technology include corn, soybean, cotton, rape and sugar beet which are tolerant to glyphosate, and which have been commercially available under a product name of RoundupReady (registered trademark), AgrisureGT, and so on. There are corn, soybean, cotton and rape which are made tolerant to glufosinate by genetic engineering technology, which have been commercially available under a product name of LibertyLink (registered trademark). A cotton made tolerant to bromoxynil by genetic engineering technology has been commercially available under a product name of BXN. There are corn and soybean which are made tolerant to both glyphosate and ALS inhibitors, examples of which include Optimum (registered trademark) GAT (registered trademark).

The aforementioned "plants" include crops genetically engineered to be able to synthesize selective toxins as known in genus *Bacillus*.

Examples of toxins expressed in such genetically engineered crops include: insecticidal proteins derived from *Bacillus cereus* or *Bacillus popilliae*; δ-endotoxins derived from *Bacillus thuringiensis* such as Cry1Ab, Cry1Ac, Cry1F, Cry1Fa2, Cry2Ab, Cry3A, Cry3Bb1, Cry9C, Cry34Ab or Cry35Ab; insecticidal proteins such as VIP1, VIP2, VIP3 or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, by using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, and so on.

Toxins contained in such genetically engineered plants are able to confer resistance particularly to insect pests belonging to Coleoptera, Diptera, Lepidoptera and Nematodes, to the plants.

Genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing Cry1Fa2 toxin and phosphinotricine N-acetyl transferase (PAT) so as to confer tolerance to glufosinate), NuCOTN33B (registered trademark) (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-tolerant trait), Agrisure (registered trademark) CB Advantage (Bt11 corn borer (CB) trait), and Protecta (registered trademark).

The aforementioned "plants" also include crops produced by using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described such as in EP-A-0 392 225, WO 95/33818 and EP-A-0 353 191.

Examples of such antipathogenic substances expressed in genetically engineered crops include: ion channel inhibitors such as a sodium channel inhibitor or a calcium channel inhibitor, among which KP1, KP4 and KP6 toxins produced by viruses have been known; stilbene synthase; bibenzyl synthase; chitinase; glucanase; a PR protein; and antipathogenic substances generated by microorganisms, such as a peptide antibiotic, an antibiotic having a hetero ring and a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, and so on.

The aforementioned "plants" also include crops to which tolerance to environmental stress such as cold tolerance, heat tolerance and desiccation tolerance has been conferred by using classical breeding methods or genetic engineering techniques. Examples of a crop to which desiccation tolerance has been conferred include a crop into which cspB gene has been introduced.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soybean having reduced linolenic content) or high-lysine (high-oil) corn (corn with increased lysine or oil content).

Stack varieties are also included in which a plurality of advantageous characters such as the classic herbicide characters mentioned above or herbicide tolerance genes, pest resistance genes, antipathogenic substance producing genes, tolerance to environmental stress, characters improved in oil stuff ingredients or characters having reinforced amino acid content are combined.

The composition of the present invention has a high pest control activity against various kinds of pests (including also Arthropod other than Insecta) while maintaining excellent safeness for mammals and crops.

The pests on which the composition of the present invention exerts an effect include, for example, arthropod such as insects and mites and specifically, those shown below.

Hemiptera:
planthoppers (Delphacidae) such as small brown planthopper (*Laodelphax striatellus*), brown rice planthopper (*Nilaparvata lugens*) and white-backed rice planthopper (*Sogatella furcifera*);
leafhoppers (Deltocephalidae) such as green rice leafhopper (*Nephotettix cincticeps*) and green rice leafhopper (*Nephotettix virescens*);
aphids (Aphididae) such as cotton aphid (*Aphis gossypii*), green peach aphid (*Myzus persicae*), cabbage aphid (*Brevicoryne brassicae*), foxglove aphid (*Macrosiphum euphorbiae*), potato aphid (*Aulacorthum solani*), oat bird-cherry aphid (*Rhopalosiphum padi*) and tropical citrus aphid (*Toxoptera citricidus*);
stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*) and tarnished plant bug (*Lygus lineolaris*);
whiteflies (Aleyrodidae) such as greenhouse whitefly (*Trialeurodes vaporariorum*), sweetpotato whitefly (*Bemisia tabaci*) and silver leaf whitefly (*Bemisia argentifolii*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), cottony-cushion scale (*Icerya purchasi*) and comstock mealybug (*Pseudococcus comstocki*); and
lace bugs (Tingidae); psyllids (Psyllidae).

Lepidoptera:
Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), European corn borer (*Ostrinia nubilalis*), cabbage webworm (*Hellula undalis*) and bluegrass webworm (*Pediasia teterrellus*);
owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plasia nigrisigna*), *Thoricoplusia* spp., *Heliothis* spp. and *Helicoverpa* spp.;
whites and sulfer butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), *Adoxophyes* spp., oriental tea tortrix (*Homona magnanima*), apple tortrix (*Archips fuscocupreanus*) and *Cydia pomonella;*
leafblotch miners (Gracillariidae) such as tea leafroller (*Caloptilia theivora*) and apple leafminer (*Phyllonorycter ringoneella*);
Carposimidae such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.;
yponomeutid moths (Yponomeutidae) such as diamondback (*Plutella xylostella*);
gelechiid moths (Gelechiidae) such as pink bollworm (*Pectinophora gossypiella*) and potato tubeworm (*Phthorimaea operculella*);
tiger moths and allies (Arctiidae) such as fall webworm (*Hyphantria cunea*); and
tineid moths (Tineidae) such as casemaking clothes moth (*Tinea translucens*) and webbing clothes moth (*Tineola bisselliella*).

Diptera:
*Culex* spp. such as common mosquito (Culex pipiens pallens), *Culex tritaeniorhynchus* and *Culex quinquefasciatus;*
*Aedes* spp. such as yellow-fever mosquito (*Aedes aegypti*) and tiger mosquito (*Aedes albopictus*);
*Anopheles* spp. such as *Anopheles sinensis;*
Chironomidae;
house flies (Muscidae) such as housefly (*Musca domestica*) and false housefly (*Muscina stabulans*);
blow flies (Calliphoridae);
flesh flies (Sarcophagidae);
little houseflies (Fanniidae),
anthomyiid flies (Anthomyiidae) such as seedcorn maggot (*Delia platura*) and onion maggot (*Delia antiqua*);
fruit flies (Tephritidae) such as melon fly (*Dacus cucurbitae*) and Mediterranean fruit fly (*Ceratitis capitata*);

vinegar flies (Drosophilidae);
moth flies (Psychodidae);
black flies (Simuliidae),
breeze flies (Tabanidae) such as horsefly (*Tabanus trigonus*);
stable flies (Stomoxyidae); and
leafminer flies (Agromyzidae) such as rice leafminer (*Agromyza oryzae*), smaller rice leafminer (*Hydrellia griseola*), rice stem maggot (*Chlorops oryzae*), legume leafminer (*Liriomyza trifolii*) and tomato leafminer (*Liriomyza sativae*).

Coleoptera:
Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squamous*), rice water weevil (*Lissorhoptrus oryzophilus*), *Anthonomus grandis*, azuki bean weevil (*Callosobruchus chinensis*), *Sphenophorus venatus*, Japanese beetle (*Popillia japonica*), cupreous chafer (*Anomala cuprea*), corn root worm (*Diabrotica* spp.), Colorado beetle (*Leptinotarsa decemlineata*), click beetle (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*) and pine shoot beetle (*Tomicus piniperda*).

Thysanoptera:
Thrips (Thripidae) such as yellow citrus thrips (*Frankliniella occidentalis*), *Thrips parmi*, yellow tea thrips (*Scirtothrips dorsalis*), onion thrip (*Thrips tabaci*), flower thrips (*Frankliniella intonsa*) and tabacco thrips (*Frankliniella fusca*).

Hymenoptera:
Cabbage sawfly (*Athalia rosae*), *Acromyrmex* spp. and fire ant (*Solenopsis* spp.).

Orthoptera:
Asiatic locust (*Locusta migratoria*), African mole cricket (*Gryllotalpa africana*), rice grasshopper (*Oxya yezoensis*), and rice grasshopper (*Oxya japonica*).

Siphonaptera:
human flea (*Pulex irritans*) and so on.

Anoplura:
body louse (*Pediculus humanus*) and so on.

Isoptera:
*Termitidae* and so on.

Dictyoptera:
Blattellidae such as German cockroach (*Blattella germanica*); and
Blattidae such as smokybrown cockroach (*Periplaneta fuliginosa*), American cockroach (*Periplaneta americana*), brown cockroach (*Periplaneta brunnea*) and oriental cockroach (*Blatta orientalis*).

Acarina:
Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*) and *Oligonychus* spp.;
eriophyid mites (Eriophyidae) such as pink citrus rust mite (*Aculops pelekassi*) and apple rust mite (*Aculus schlechtendali*);
tarosonemid mites (Tarsonemidae) such as broad mite (*Polyphagotarsonemus latus*);
false spider mites (Tenuipalpidae); Tuckerellidae; ticks (Ixodidae) such as *Haemaphysalis longicornis*, *Haemaphysalis flava*, *Dermacentor taiwanicus*, *Ixodes ovatus*, *Ixodes persulcatus* and *Boophilus microplus*;
acarid mites (Acaridae) such as mold mite (*Tyrophagus putrescentiae*);
house dust mites (Pyroglyphidae) such as *Dermatophagoides farinae* and *Dermatophagoides ptrenyssnus*;
cheyletide mites (Cheyletidae) such as *Cheyletus eruditus*, *Cheyletus malaccensis* and *Cheyletus moorei*; and
parasitoid mites (Dermanyssidae).

EXAMPLES

The present invention will be illustrated further in detail by formulation examples, seed treatment examples and test examples shown below, but the present invention is not limited only to the following examples. In the following examples, the part represents part by weight unless otherwise stated. The compounds (1) to (34) correspond to compound numbers described in Tables 1 and 2 mentioned above.

Formulation Example 1

Fifty (50) parts of any of the compounds (1) to (34), 0.5 parts of pyriproxyfen, 38.5 parts of NN kaolin clay (manufactured by Takehara Kagaku Kogyo Co., Ltd.), 10 parts of Morwet D425 (product name, manufactured by AkzoNobel) and 1.5 parts of Morwet EFW (product name, manufactured by DESOTO) are mixed, to obtain an AI premix. This premix is ground with a jet mill to obtain respective powders.

Formulation Example 2

One (1) part of any of the compounds (1) to (34), 4 parts of pyriproxyfen, 1 part of synthetic hydrated silicon oxide, 2 parts of calcium ligninsulfonate, 30 parts of bentonite and 62 parts of kaolin clay are fully ground and mixed, and the resultant mixture is added with water and fully kneaded, and then subjected to granulation and drying to obtain respective granules.

Formulation Example 3

One (1) part of any of the compounds (1) to (34), 40 parts of pyriproxyfen, 3 parts of calcium ligninsulfonate, 2 parts of sodium laurylsulfate and 54 parts of synthetic hydrated silicon oxide are fully ground and mixed to obtain respective wettable powders.

Formulation Example 4

One (1) part of any of the compounds (1) to (34), 2 parts of pyriproxyfen, 85 parts of kaolin clay and 10 parts of talc are fully ground and mixed to obtain respective powders.

Formulation Example 5

Two (2) parts of any of the compounds (1) to (34), 0.25 parts of pyriproxyfen, 14 parts of polyoxyethylene styrylphenyl ether, 6 parts of calcium dodecylbenzenesulfonate and 77.75 parts N-methylpyrrolidone are fully mixed to obtain respective emulsions.

An effect of the composition of the present invention on control of pests will be illustrated in examples below.

Test Example 1: Pesticidal Effect on *Plutella xylostella* by Bait Crop Immersion Treatment To 10 mg of the compound (1) was added 0.2 ml of acetone containing 5% of Tween 20 (product name: SOLGEN (registered trademark) TW-20, manufactured by Dai-ichi Kogyo Seiyaku Co., Ltd.) to cause dissolution, and the solution was diluted with a 5,000-fold diluted solution of a spreading agent (product name: Dine (registered trademark), manufactured by Sumitomo Chemical Garden Products Inc.) to prepare a diluted liquid of the compound (1). A commercially available pyriproxyfen emulsifiable concentrate manufactured by Sumitomo Chemical Co., Ltd. under the product name of Lano (registered trademark) emulsifiable concentrate was diluted with a 5,000-fold diluted solution of a spreading agent (product name: Dine (registered trademark), manufactured by Sumitomo Chemical Garden Products Inc.) to prepare a diluted liquid of pyriproxyfen. These diluted liquids were mixed to prepare a test solution of prescribed concentration. In the test solution, one true leaf of *Brassicae oleracea* at 7 to 8-leaves stage was immersed for several seconds, and air-dried. After drying of the test solution, this leaf was placed in a polyethylene cup (200-ml volume), and ten third-instar larvae of *Plutella xylostella* were released. The cup was stored in a constant temperature breeding room (25° C.), and the number of dead larvae was counted 2 days after, and the mortality was determined by the following equation [1].

Mortality (%)=(dead larvae number/tested larvae number)×100  Equation [1]

The results are shown in Table 3.

TABLE 3

| | Test compounds | Mortality(%) |
|---|---|---|
| Example 1 | compound (1) 0.05 ppm + pyriproxyfen 0.8 ppm | 90 |
| Example 2 | compound (1) 0.05 ppm + pyriproxyfen 0.05 ppm | 90 |
| Example 3 | compound (1) 0.1 ppm + pyriproxyfen 0.1 ppm | 100 |

Test Example 2: Pesticidal Effect on *Plutella xylostella* by Bait Crop Immersion Treatment To 10 mg of the compound (13) was added 0.2 ml of acetone containing 5% of Tween 20 (product name: SOL-GEN (registered trademark) TW-20, manufactured by Dai-ichi Kogyo Seiyaku Co., Ltd.) to cause dissolution, and the solution was diluted with a 5.000-fold diluted solution of a spreading agent (product name: Dine (registered trademark), manufactured by Sumitomo Chemical Garden Products Inc.) to prepare a diluted liquid of the compound (13). A commercially available pyriproxyfen emulsifiable concentrate manufactured by Sumitomo Chemical Co., Ltd. under the product name of Lano (registered trademark) emulsifiable concentrate was diluted with a 5.000-fold diluted solution of a spreading agent (product name: Dine (registered trademark), manufactured by Sumitomo Chemical Garden Products Inc.) to prepare a diluted liquid of pyriproxyfen. These diluted liquids were mixed to prepare a test solution of prescribed concentration. In the test solution, one true leaf of *Brassicae oleracea* at 7 to 8-leaves stage was immersed for several seconds, and air-dried. After drying of the test solution, this leaf was placed in a polyethylene cup (200-ml volume), and ten third-instar larvae of *Plutella xylostella* were released. The cup was stored in a constant temperature breeding room (25° C.), and the number of dead larvae was counted 6 days after, and the mortality was determined by the above equation [1].

The results are shown in Table 4.

TABLE 4

| | Test compounds | Mortality(%) |
|---|---|---|
| Comparative Example 4-1 | compound (13) 0.013 ppm | 20 |

TABLE 4-continued

| | Test compounds | Mortality(%) |
|---|---|---|
| Comparative Example 4-2 | pyriproxyfen 0.8 ppm | 40 |
| Example 4 | compound (1) 0.013 ppm + pyriproxyfen 0.8 ppm | 100 |

Test Example 3: Pesticidal Effect on *Spodoptera litura* by Bait Crop Immersion Treatment To 10 mg of the compound (13) or (15) was added 0.2 ml of acetone containing 5% of Tween 20 (product name: SOL-GEN (registered trademark) TW-20, manufactured by Dai-ichi Kogyo Seiyaku Co., Ltd.) to cause dissolution, and the solution was diluted with a 5,000-fold diluted solution of a spreading agent (product name: Dine (registered trademark), manufactured by Sumitomo Chemical Garden Products Inc.) to prepare a diluted liquid of the compound. A commercially available pyriproxyfen emulsifiable concentrate manufactured by Sumitomo Chemical Co., Ltd. under the product name of Lano (registered trademark) emulsifiable concentrate was diluted with a 5,000-fold diluted solution of a spreading agent (product name: Dine (registered trademark), manufactured by Sumitomo Chemical Garden Products Inc.) to prepare a diluted liquid of pyriproxyfen. These diluted liquids were mixed to prepare a test solution of prescribed concentration. In the test solution, one true leaf of *Brassicae oleracea* at 7 to 8-leaves stage was immersed for several seconds, and air-dried. After drying of the test solution, this leaf was placed in a polyethylene cup (200-ml volume), and ten fourth-instar larvae of *Spodoptera litura* were released. The cup was stored in a constant temperature breeding room (25° C.), and the number of dead larvae was counted 2 days after, and the mortality was determined by the above equation [1].

The results are shown in Table 5.

TABLE 5

| | Test compounds | Mortality(%) |
|---|---|---|
| Comparative Example 5-1 | compound (13) 0.05 ppm | 20 |
| Comparative Example 5-2 | pyriproxyfen 0.2 ppm | 30 |
| Example 5 | compound (13) 0.05 ppm + pyriproxyfen 0.2 ppm | 70 |
| Comparative Example 6-1 | compound (15) 1.56 ppm | 50 |
| Comparative Example 6-2 | pyriproxyfen 3.13 ppm | 50 |
| Example 6 | compound (15) 1.56 ppm + pyriproxyfen 3.13 ppm | 100 |
| Comparative Example 7-1 | compound (15) 1.56 ppm | 50 |
| Comparative Example 7-2 | pyriproxyfen 0.2 ppm | 30 |
| Example 7 | compound (15) 1.56 ppm + pyriproxyfen 0.2 ppm | 100 |

By use of the amide compound (I) with pyriproxyfen in admixture, a higher Pesticidal efficacy is exerted on *Plutella xylostella*.

INDUSTRIAL APPLICABILITY

According to the present invention, it becomes possible to provide a pest control composition showing an excellent efficacy for controlling pests.

The invention claimed is:

1. A pest control composition comprising, as active ingredients, the following (A) and (B):
   (A) an amide compound of the formula (I):

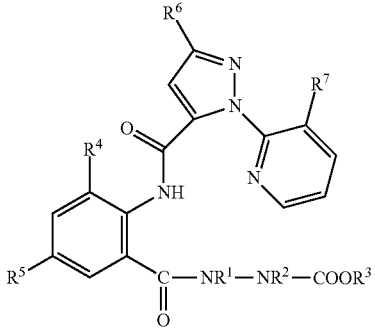

wherein $R^1$ is an ethyl group, $R^2$ is a hydrogen atom or an ethyl group, $R^3$ is a methyl group, $R^4$ is a chlorine atom, a bromine atom or a methyl group, $R^5$ is a chlorine atom, a bromine atom or a cyano group, $R^6$ is a chlorine atom, a bromine atom or a trifluoromethyl group and $R^7$ is a chlorine atom; and
   (B) pyriproxyfen.

2. The pest control composition according to claim 1, comprising a weight ratio of the ingredient (A) to the ingredient (B) of 10:90 to 90:10.

3. The pest control composition according to claim 1, wherein the (A) amide compound of the formula (I) is selected from the group consisting of
   (i) a compound of formula (I), wherein $R^1$ is an ethyl group, $R^2$ is a hydrogen atom, $R^3$ is a methyl group, $R^4$ is a bromine atom, $R^5$ is a bromine atom, $R^6$ is a bromine atom and $R^7$ is a chlorine atom;
   (ii) a compound of formula (I), wherein $R^1$ is an ethyl group, $R^2$ is an ethyl group, $R^3$ is a methyl group, $R^4$ is a bromine atom, $R^5$ is a bromine atom, $R^6$ is a bromine atom and $R^7$ is a chlorine atom; and
   (iii) a compound of formula (I), wherein $R^1$ is an ethyl group, $R^2$ is a hydrogen atom, $R^3$ is a methyl group, $R^4$ is a methyl group, $R^5$ is a cyano group, $R^6$ is a bromine atom and $R^7$ is a chlorine atom.

4. A method for controlling an insect pest, comprising applying an effective amount of the insect pest control composition according to claim 1 to the insect pest, a habitat of the insect pest, or a plant to be protected from damage by the insect pest.

* * * * *